United States Patent
Broussard et al.

(10) Patent No.: US 6,281,295 B1
(45) Date of Patent: *Aug. 28, 2001

(54) ENAMINES AS VULCANIZATION ACCELERATORS FOR NATURAL OR SYNTHETIC RUBBERS

(75) Inventors: Fabio Broussard, Brusaporto; Mauro Adovasio; José Roncalli, both of Bergamo; Gianbattista Taroni, Mozzo; Corrado Callierotti, Seriate, all of (IT)

(73) Assignee: Great Lakes Chemical Italia S.r.l., Milan (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/961,497

(22) Filed: Oct. 30, 1997

Related U.S. Application Data

(63) Continuation of application No. 08/625,554, filed on Mar. 29, 1996, now abandoned.

(30) Foreign Application Priority Data

Mar. 31, 1995 (IT) .............................................. MI95A0649

(51) Int. Cl.$^7$ ....................................................... C08F 8/30
(52) U.S. Cl. .................. 525/293; 525/329.3; 525/332.6; 525/347; 525/374
(58) Field of Search .............................. 525/332.6, 329.3, 525/293, 374, 347

(56) References Cited

U.S. PATENT DOCUMENTS 1,780,334 * 11/1930 Burnett .
4,082,706 4/1978 Danielson .

FOREIGN PATENT DOCUMENTS 0 634 448    1/1995 (EP) .

OTHER PUBLICATIONS

Chem Abst, 84:4878z (1976).*
Chem Abst, 88:22305x (1978).*
Chem Abst, 104:50616s (1986).*
Chemical Abstracts, vol. 112, No. 10, AN 79168, Mar. 5, 1990, JP–A–01 172 437, Jul. 7, 1989.
Organikum, pp. 479–482, 1977, "Reaktionen Von Aldehyden Und Ketonen Mit Aminoverbindungen".
Rubber Journal, vol. 154, No. 1, pp. 24 and 26, Jan. 1, 1972, S.H. Morrell, et al., "Accelerators Based on Phenyl–β–Aminoketones".
Y, Kawaoka, "Recent Problems in Vulcanisation", Nippon Gomu Kyokaisha, 1981, No. 8, p. 517.
Kirk–Othmer Encyclopedia, vol. 20, pp. 335–360.
Kirk–Othmer Encyclopedia, 4$^{th}$ Edition, vol. 21, pp. 460–464 and 468.

* cited by examiner

Primary Examiner—Bernard Lipman
(74) Attorney, Agent, or Firm—Oblon, Spivak, McClelland, Maier & Neustadt, P.C.

(57) ABSTRACT

Vulcanization accelerators consisting of compounds belonging to the group of enamines having general formula (I):

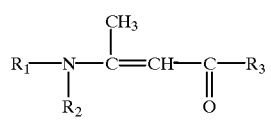

(I)

13 Claims, 4 Drawing Sheets

ENAMINES AS VULCANIZATION ACCELERATORS FOR NATURAL OR SYNTHETIC RUBBERS

Figure 1:
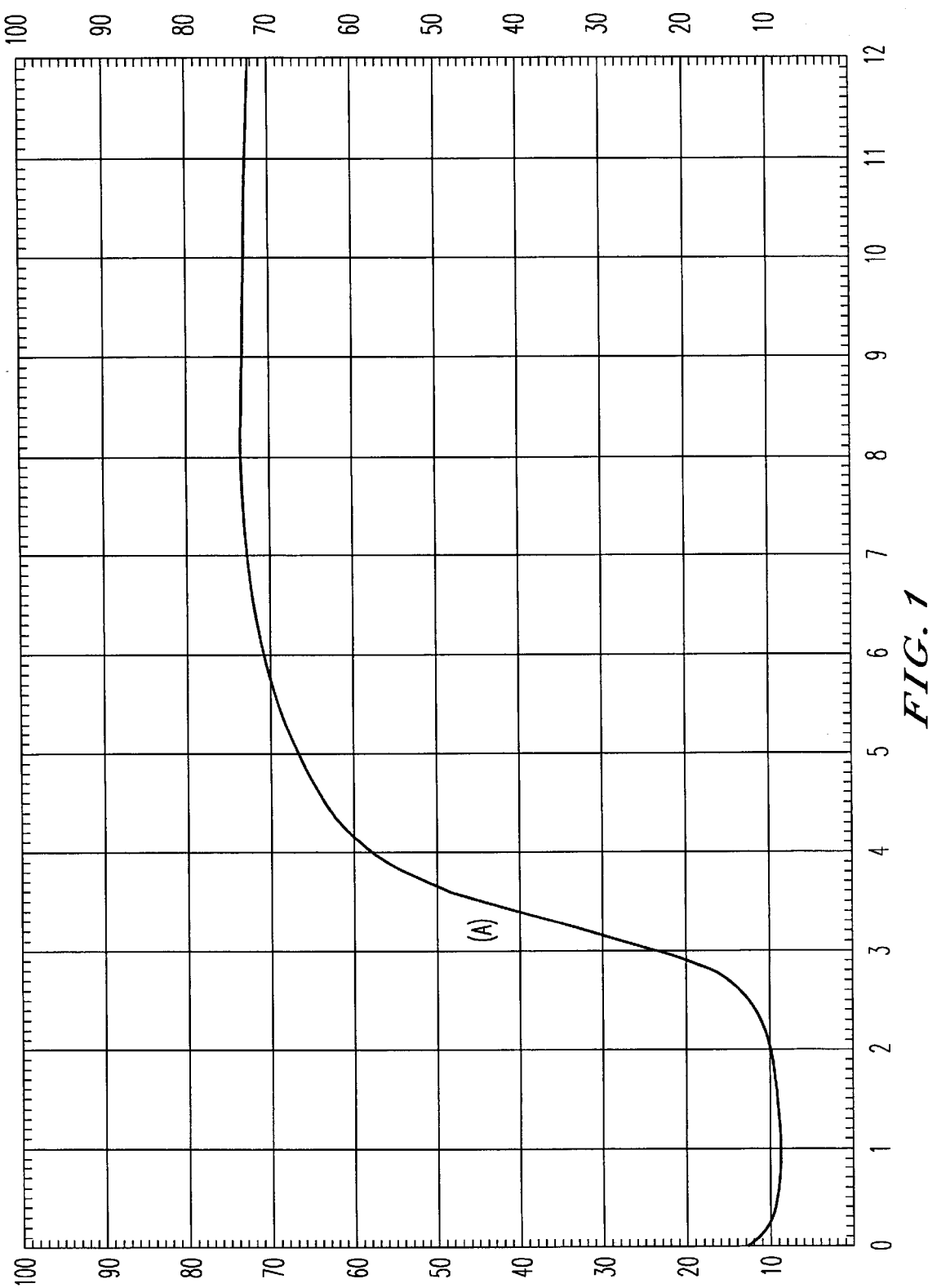

This application is a Continuation of application Ser. No. 08/625,554, filed on Mar. 29, 1996, now abandoned.

BACKGROUND OF THE INVENTION

1. Field of the Invention

The present invention relates to vulcanization accelerators consisting of compounds belonging to the group of enamines.

More specifically, the present invention relates to vulcanization accelerators consisting of compounds, deriving from primary or secondary aliphatic amines, belonging to the group of enamines and a process for their preparation.

2. Discussion of the Background

It is known that the vulcanization of natural or synthetic rubbers takes place by the cross-linking between polymeric chains owing to the use of sulfur or peroxides.

The vulcanization process in the presence of sulfur has been optimized by the use of accelerators capable of limiting the vulcanization times and guaranteeing repeated results with respect to the properties of the end-products.

There are many known products which are used as vulcanization accelerators as described, for example, by Kirk-Othmer: "Encyclopedia of Chemical Technology", Vol. 20, pages 337–364. Among these mercaptobenzothiazol and its sulfenamides, dithiocarbamates and thiuram disulfides, can be mentioned.

Frequently, in order to obtain good results, these products are not used alone but are combined with each other.

Among vulcanization accelerators there is a group of products defined as secondary accelerators, used as activators of primary accelerators with a thiazole base. Examples of these products are: N,N'-diphenylguanidine (DPG), N,N'-diortho-toluylguanidine (DOTG), 2,4,6-tris-dimethylaminomethylphenol and the condensation products of aromatic amines with aliphatic aldehydes.

European patent application 634.448, filed by the Applicant, describes vulcanization accelerators consisting of compounds belonging to the group of enamines having the following general formula:

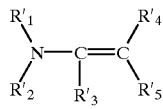

wherein:

R'$_1$ and R'$_2$, the same or different, represent a C$_1$–C$_{18}$ alkyl group, linear or branched; a C$_2$–C$_{18}$ alkenyl group; a C$_3$–C$_8$ cycloalkyl group; a C$_6$–C$_{18}$ aryl group; a C$_7$–C$_{20}$ alkylaryl or arylalkyl group; or R'$_1$ and R'$_2$, considered jointly with the nitrogen atom, represent a C$_3$–C$_8$ heterocyclic group possibly containing a second heteroatom selected from O, S and N;

R'$_3$ and R'$_4$, the same or different, represent a hydrogen atom; a C$_1$–C$_{18}$ alkyl group, linear or branched; a C$_2$–C$_{18}$ alkenyl group; a C$_6$–C$_{18}$ aryl group; a C$_7$–C$_{20}$ alkylaryl or arylalkyl group; or R'$_3$ and R'$_4$, considered jointly with the double bond C=C to which they are linked, represent a C$_3$–C$_{12}$ cycloalkenyl group;

R'$_5$ represents a hydrogen atom; a C$_1$–C$_{18}$ alkyl group, linear or branched; a C$_2$–C$_{18}$ alkenyl group; or, when R'$_3$ represents a hydrogen atom, a linear or branched C$_1$–C$_{18}$ alkyl group, a C$_2$–C$_{18}$ alkenyl group, a C$_6$–C$_{18}$ aryl group or a C$_7$–C$_{20}$ alkylaryl or arylalkyl group, R'$_4$ and R'$_5$, considered jointly with the carbon atom which has the double bond C=C, represent a C$_3$–C$_{12}$ cycloalkylene group.

The Applicant has now found compounds, deriving from primary or secondary aliphatic amines, belonging to the group of enamines, which can be used as vulcanization accelerators and have improved properties with respect to those known in the art. In fact, the above enamines are less volatile, are not irritating and generally have no odour.

SUMMARY OF THE INVENTION AND BRIEF DESCRIPTION OF THE DRAWINGS

The present invention therefore relates to vulcanization accelerators consisting of compounds belonging to the group of enamines having general formula (I):

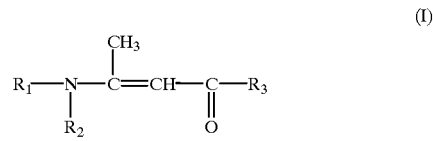

wherein:

R$_1$ and R$_2$, the same or different, represent a hydrogen atom; a C$_1$–C$_{18}$ alkyl group, linear or branched; a C$_2$–C$_8$ alkoxyalkyl group, linear or branched; a C$_3$–C$_8$ cycloalkyl group possibly containing a heteroatom selected from oxygen, nitrogen and sulfur; a C$_7$–C$_{20}$ arylalkyl group; or R$_1$ and R$_2$, considered jointly with the nitrogen atom, represent a C$_3$–C$_8$ heterocyclic group possibly containing a second heteroatom selected from oxygen, nitrogen and sulfur;

R$_3$ represents a C$_1$–C$_{18}$ alkyl group, linear or branched; a C$_6$–C$_{18}$ aryl group; a C$_7$–C$_{20}$ alkylaryl or arylalkyl group; a C$_1$–C$_8$ alkoxyl group linear or branched.

Examples of R$_1$ and R$_2$ radicals, apart from the hydrogen atom, are methyl, ethyl, propyl, butyl, octyl, cyclohexyl, benzyl, methoxyethyl, etc.

Examples of C$_3$–C$_8$ heterocyclic groups, when R$_1$ and R$_2$ are considered jointly with the nitrogen atom, are morpholine, pyrrolidine, piperidine, piperazine, thiomorpholine, thiazolidine, benzothiazolidine, etc.

Examples of R$_3$ radicals are methyl, ethyl, propyl, phenyl, oxymethyl, oxyethyl, etc.

Figure 2:
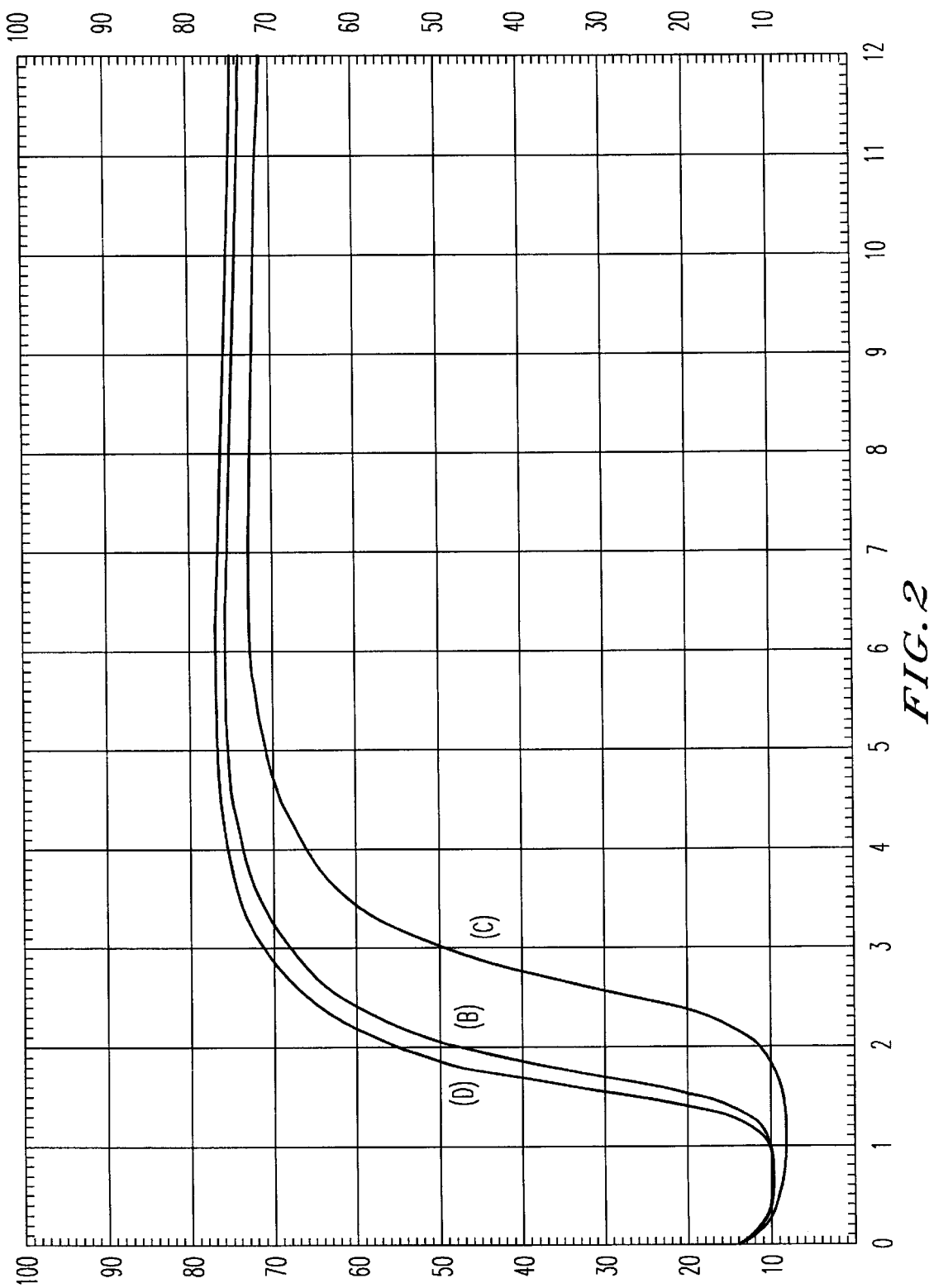
Figure 3:
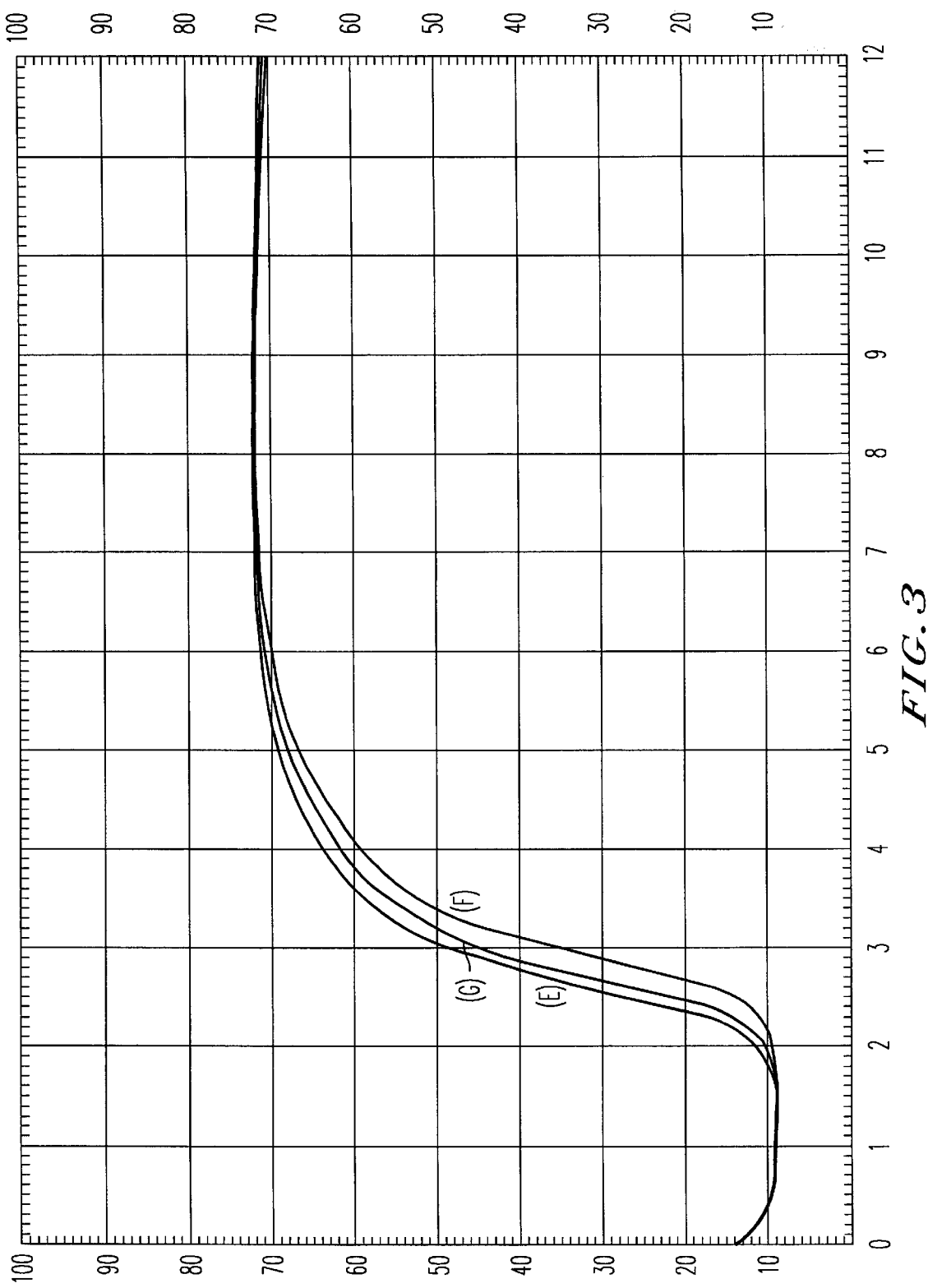
Figure 4:
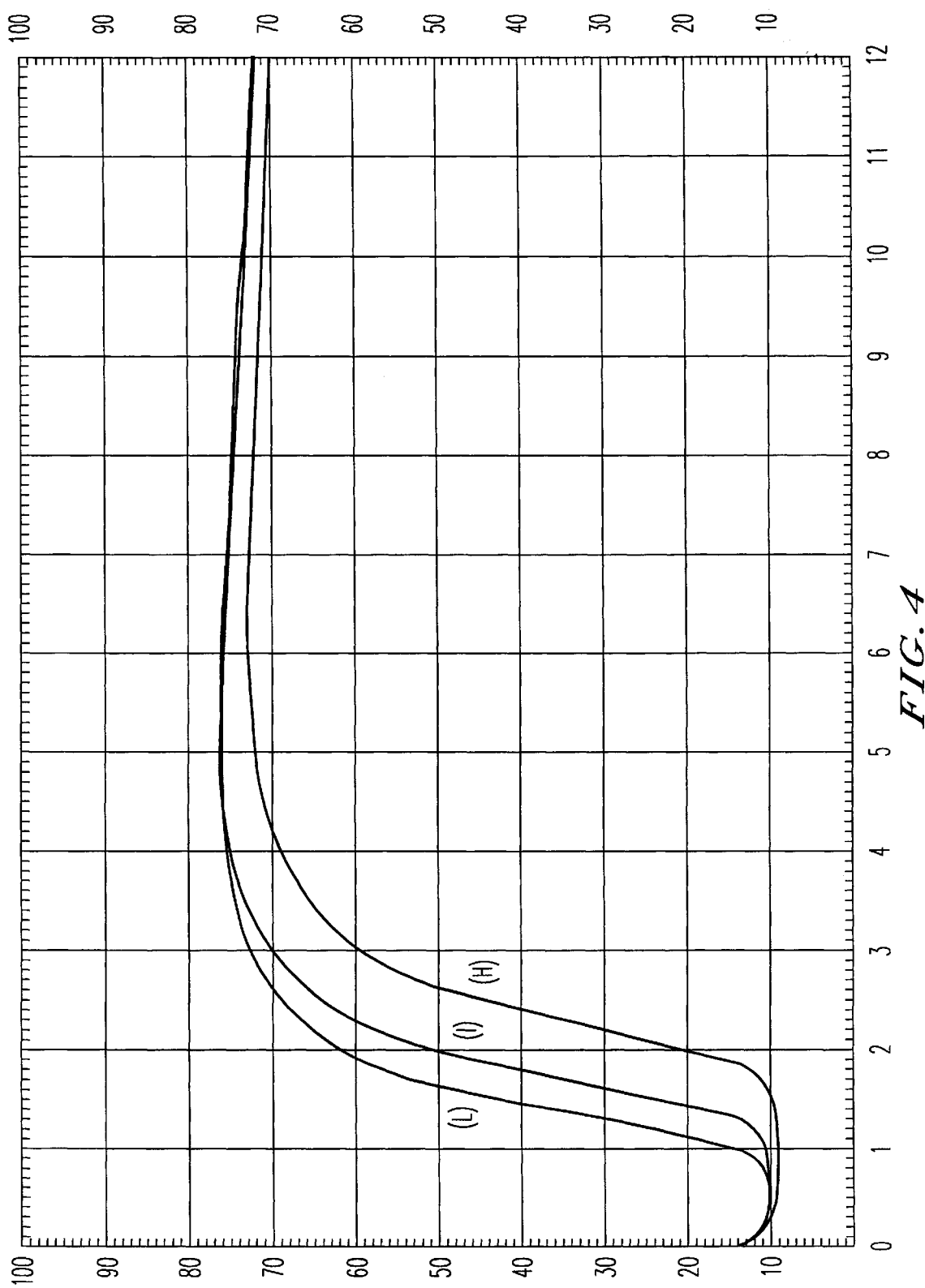

The capacity of the compounds having general formula (I) to act as vulcanization accelerators was shown by rheometric curves which are indicated in FIGS. 2–4 (the time is indicated in abscissa; the torque in ordinate; the meanings of the letters appearing on the rheometrical curves will be provided later) obtained by measuring the stress of an oscillating disk englobed in a rubber sample during vulcanization. The rheometrical curves were determined using a Rheometer 100 of Monsanto.

The compounds having general formula (I) can be used alone or combined with other vulcanization accelerators such as, for example, mercapto-benzothiazole sulfenamides.

FIGS. 1–4 show the rheometrical curves obtained using N-cyclohexyl-2-mercapto-benzothiazole sulfenamide (CBS) alone or combined with a compound having general formula (I). These curves indicate that, when CBS is used in combination with a compound having general formula (I), the time for reaching 90% of the maximum vulcanization curve t$_c$(90), is considerably shortened thus allowing a more rapid vulcanization kinetics compared to CBS alone.

A further object of the present invention is a process for the synthesis of compounds having general formula (I).

A process for the synthesis of the compounds having general formula (I) described above comprises the reaction of 1 mole of a primary or secondary, aliphatic amine, having general formula (II):

wherein $R_1$ and $R_2$ have the same meaning described above, with 1 mole of a β-ketoester or of a 1,3-diketone having general formula (III):

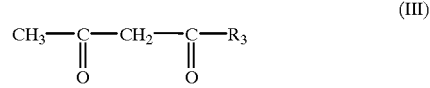

wherein $R_3$ has the same meaning described above.

The above reaction takes place in the presence of an organic solvent, preferably a hydrocarbon, in particular toluene, at a temperature of between 60° C. and 160° C., preferably between 115° C. and 150° C., at atmospheric pressure and for a time of between 0.5 and 24 hours, preferably between 3 and 10 hours. Acetic acid can be added to this reaction as catalyst.

During the above reaction, reaction water is released which is separated by azeotropic distillation using an apparatus for azeotropic distillation, whereas the organic solvent is recycled.

At the end of the reaction, the solvent and possible acetic acid present, are removed by distillation, thus obtaining a raw product. The enamine having general formula (I) is purified from the raw product thus obtained by fractional distillation, operating under vacuum, at a pressure of between 0.1 mm/Hg and 50 mm/Hg and at a temperature of between 40° C. and 200° C.

Further processes for the synthesis of compounds having general formula (I) are described however in literature, for example in Houben-Weil (1957), Vol. 11/1, pages 172–178.

Primary or secondary, aliphatic amines having general formula (II) which can be used for the purposes of the present invention are cyclohexylamine, tert-butylamine, tert-octylamine, benzylamine, 2-methoxyethylamine, 2-furfurylamine, pyrrolidine, piperidine, morpholine, dibenzylamine, etc.

β-ketoesters or 1,3-diketones having general formula (III) which can be used for the purposes of the present invention are ethyl acetoacetate, acetylacetone, benzoylacetone, p-toluylacetone, etc.

The enaminic function of the compounds having general formula (I) synthesized by the above process, is confirmed by analysis via NMR spectrometry (obtained using a BRUKER AC 200 spectrometer) carried out on samples with a high purity (GC>95% confirmed by gas chromatography), in which there is inequivocably the presence of the N—H group and double bond C═C and the absence of the double bond N═C typical of Schiff bases. In the following examples the NMR spectra are indicated only of the compounds having general formula (I) wherein $R_1$ or $R_2$ represent hydrogen, as these compounds, because they derive from the reaction of primary amines with β-ketoesters or 1,3-diketones, could be Schiff bases.

On the contrary, in the case of compounds having general formula (I) which derive from the reaction of secondary amines with β-ketoesters or 1,3-diketones, it is not necessary to indicate the NMR spectrum as only enamines can be obtained from this reaction.

The vulcanization accelerators having general formula (I) can be used in both natural and synthetic rubbers such as, for example, SBR, NBR, BR, EPDM, etc.

DESCRIPTION OF THE PREFERRED EMBODIMENTS

Some illustrative examples are given below to provide a better understanding of the present invention and for its embodiment but these should in no way be considered as limiting the scope of the invention itself.

EXAMPLE 1

Preparation of ethyl β-cyclohexylamine crotonate (Compound Nr. 1)

99.18 g (1 mole) of cyclohexylamine, 200 g of toluene, 130.14 g of ethyl acetoacetate (1 mole) and 2.08 g of glacial acetic acid are charged into a 1 liter, 4-necked reactor, equipped with a mechanical stirrer, thermometer and reflux condenser with a water separator.

The reaction mass is maintained under stirring and reflux heated for 4 hours at 115° C.–118° C. During this period reaction water is formed which is separated by azeotropic distillation: 19.2 g of reaction water are separated.

The solvent and acetic acid are removed by distillation and the raw residue thus obtained is subjected to fractional distillation.

This distillation is carried out in a still consisting of a 500 ml boiler equipped with a thermometer, stirrer, column, condenser and device for collecting the fractions.

A central fraction containing 205.8 g of distilled product, corresponding to Compound Nr. 1 is collected from the above distillation, operating under the following conditions:

temperature at the top: 145° C.–153° C.;

temperature of the boiler: 170° C.–180° C.;

vacuum: 30–32 mm/Hg.

Compound Nr. 1 thus obtained is analyzed by gas-chromatography (GC) and is found to have a purity of 98.3% with a yield of about 97.8%.

Compound Nr. 1 is characterized by NMR analysis. The enamine structure of Compound Nr. 1 is proved by NMR analysis in which the presence of the N—H group and double bond C═C is shown by the chemical shift.

$^1$H-NMR (200 MHz, CDCl$_3$-TMS) δ (ppm): 8.57–8.54 (N—H); 4.30 (H—C).

$^{13}$C-NMR (50 MHz, CDCl$_3$-TMS) δ (ppm): 160.58 (C'); 81.58 (C").

The carbon atoms indicated by (C') and (C"), in this example and in the following examples, indicate the presence of the double bond C═C:

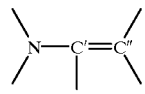

The other compounds (Compounds 2–10) are prepared similarly to example 1, of which only the reaction conditions and characteristics are provided.

EXAMPLE 2

Preparation of ethyl β-benzylamine crotonate (Compound Nr. 2)

Amine: benzylamine; 107.16 g (1 mole).

Carbonylic compound: ethyl acetoacetate; 130.14 g (1 mole)

Solvent: toluene; 200 g.

Catalyst: acetic acid; 2.08 g.

Reaction water separated: 19.8 g.

Reaction time and temperature: 5 hours at 120°–124° C.

Distillation range: 148° C.–156° C. (top) ; 170° C.–185° C. (boiler); 20 mm/Hg (vacuum).

Product obtained: 206.4 g.

Purity GC: 98.0%.

Yield: 94.1%.

$^1$H-NMR (200 MHz, CDCl$_3$-TMS) δ (ppm): 8.95 (N—H); 4.52 (H—C).

$^{13}$C-NMR (50 MHz, CDCl$_3$-TMS) δ (ppm): 161.54 (C'); 83.05 (C").

EXAMPLE 3

Preparation of 2-tert-octylamino-penten-(2)-one-(4) (Compound Nr. 3)

Amine: tert-octylamine; 129.25 g (1 mole).

Carbonylic compound: acetylacetone; 100.12 g (1 mole)

Solvent: toluene; 100 g.

Catalyst: acetic acid; 2.33 g.

Reaction water separated: 19.7 g.

Reaction time and temperature: 10 hours at 123°–134° C.

Distillation range: 113° C.–117°C. (top) ; 125° C.–135° C. (boiler); 0.3–1.0 mm/Hg (vacuum).

Product obtained: 156.1 g.

Purity GC: >99.0%.

Yield: 73.8%.

$^1$H-NMR (200 MHz, CDCl$_3$-TMS) δ (ppm): 11.33 (N—H); 4.79 (H—C).

$^{13}$C-NMR (50 MHz, CDCl$_3$-TMS) δ (ppm): 162.90 (C'); 96.06 (C").

EXAMPLE 4

Preparation of 2-cyclohexylamino-penten-(2)-one-(4) (Compound Nr. 4)

Amine: cyclohexylamine; 99.18 g (1 mole).

Carbonylic compound: acetylacetone; 100.12 g (1 mole)

Solvent: toluene; 100 g.

Catalyst: acetic acid; 2.33 g.

Reaction water separated: 18.0 g.

Reaction time and temperature: 3 hours at 120°–138° C.

Distillation range: 105° C.–125° C. (top); 114° C.–126° C. (boiler); 0.2–0.7 mm/Hg (vacuum).

Product obtained: 175.3 g.

Purity GC: >99.0%.

Yield: 96.7%.

$^1$H-NMR (200 MHz, CDCl$_3$-TMS) δ (ppm): 10.83–10.85 (N—H); 4.75 (H—C).

$^{13}$C-NMR (50 MHz, CDCl$_3$-TMS) δ (ppm): 161.43 (C'); 94.57 (C").

EXAMPLE 5

Preparation of ethyl β-morpholine crotonate (Compound Nr. 5)

Amine: morpholine; 87.12 g (1 mole).

Carbonylic compound: ethyl acetoacetate; 130.14 g (1 mole)

Solvent: toluene; 200 g.

Catalyst: acetic acid; 2.08 g.

Reaction water separated: 23.1 g.

Reaction time and temperature: 7 hours at 119°–120° C.

Distillation range: 130° C.–138° C. (top) ; 145° C.–160° C. (boiler); 0.5–1.0 mm/Hg (vacuum).

Product obtained: 148.1 g.

Purity GC: 86.5%.

Yield: 64.3%.

EXAMPLE 6

Preparation of ethyl β-piperidine crotonate (Compound Nr. 6)

Amine: piperidine; 85.15 g (1 mole).

Carbonylic compound: ethyl acetoacetate; 130.14 g (1 mole)

Solvent: toluene; 200 g.

Catalyst: acetic acid; 2.08 g.

Reaction water separated: 17.9 g.

Reaction time and temperature: 6 hours at 121°–122° C.

Distillation range: 124° C.–133° C. (top); 155° C.–180° C. (boiler); 0.5–1.0 mm/Hg (vacuum).

Product obtained: 168.0 g.

Purity GC: 88.0%.

Yield: 74.9%.

EXAMPLE 7

Preparation of 2-piperidino-penten-(2)-one-(4) (Compound Nr. 7)

Amine: piperidine; 85.15 g (1 mole).

Carbonylic compound: acetylacetone; 100.12 g (1 mole)

Solvent: toluene; 100 g.

Catalyst: acetic acid; 2.33 g.

Reaction water separated: 24.4 g.

Reaction time and temperature: 10 hours at 128°–134° C.

Distillation range: 140° C.–190° C. (top); 170° C.–196° C. (boiler); 30 mm/Hg (vacuum).

Product obtained: 151.7 g.

Purity GC: >94.9%.

Yield: 90.7%

EXAMPLE 8

Preparation of ethyl β-pyrrolidino crotonate (Compound Nr. 8)

Amine: pyrrolidine; 71.12 g (1 mole).

Carbonylic compound: ethyl acetoacetate; 130.14 g (1 mole)

Solvent: toluene; 100 g.

Catalyst: absent.

Reaction water separated: 18.8 g.

Reaction time and temperature: 3 hours at 136°–140° C.

Distillation range: 120° C.–138° C. (top); 124° C.–142° C. (boiler); 0.2–0.5 mm/Hg (vacuum).

Product obtained: 172.1 g.

Purity GC: 99.1%.

Yield: 93.9%.

EXAMPLE 9

Peparation of 2-pyrrolidino-penten-(2)-one-(4) (Compound Nr. 9)

Amine: pyrrolidine; 71.12 g (1 mole).

Carbonylic compound: acetylacetone; 100.12 g (1 mole)

Solvent: toluene; 100 g.

Catalyst: absent.
Reaction water separated: 19.1 g.
Reaction time and temperature: 5 hours at 122°–133° C.
Distillation range: 124° C.–140° C. (top); 140° C.–145° C. (boiler); 0.2–0.5 mm/Hg (vacuum).
Product obtained: 129.8 g.
Purity GC: >99.0%.
Yield: 84.7%.

EXAMPLE 10

Preparation of ethyl β-(2-methoxyethylamino)-crotonate (Compound Nr.10)

Amine: 2-methoxyethylamine; 75.11 g (1 mole).
Carbonylic compound: ethyl acetoacetate; 130.14 g (1 mole)
Solvent: toluene; 100 g.
Catalyst: acetic acid; 2.33 g.
Reaction water separated: 20.2 g.
Reaction time and temperature: 4 hours at 130°–150° C.
Distillation range: 89° C.–92° C. (top); 110° C.–130° C. (boiler); 0.1–0.2 mm/Hg (vacuum).
Product obtained: 153 g.
Purity GC: >99.%.
Yield: 81.7%.
$^1$H-NMR (200 MHz, CDCl$_3$-TMS) δ (ppm): 8.58 (N—H); 4.36 (H—C).
$^{13}$C-NMR (50 MHz, CDCl$_3$-TMS) δ (ppm): 161.36 (C'); 82.50 (C").

EXAMPLES 11–21

Examples 11–21 illustrate the behaviour of the compounds having general formula (I) in combination with N-cyclohexyl-2-mercapto-benzothiazole sulfenamide (CBS).

Mixtures based on natural rubber were prepared, of which the components are shown in Table 1.

TABLE 1

| COMPONENTS | WEIGHT %* |
|---|---|
| Natural rubber SMR 10 | 100.00 |
| Zinc Oxide | 5.00 |
| Stearine | 1.00 |
| Highly aromatic oil | 5.00 |
| Carbon black N 375 | 45.00 |
| Sulfur | 2.00 |
| CBS | 1.00 |
| Compounds with formula (I) ** | 0.50 |

*weight % with respect to the rubber.
**Compounds Nr. 1–10.

The Monsanto Rheometer is used under the following operating conditions:
oscillation arc: ±1;
temperature: 150° C.

The t$_c$ (90) were calculated on the resulting rheometric curves, shown in FIGS. 1–4, and the values are given in Table 2. The rheometric curves indicated in FIGS. 2–4, clearly show the efficiency of the compounds having general formula (I) as vulcanization accelerators. This efficiency is also evident from the t$_c$ (90) values shown in Table 2 in which it can be seen that the T$_c$(90) values of the mixtures containing CBS and the compounds having general formula (I) are always lower than the t$_c$(90) of the mixture containing CBS alone.

FIG. 1 shows the rheometrical curve of CBS alone corresponding to: EX.11: (A).

In FIG. 2 the letters appearing on the rheometrical curves indicate the following compounds with formula (I):
EX. 17: (B) ethyl β-piperidino crotonate (Compound Nr. 6);
EX. 12: (C) ethyl β-cyclohexylamino crotonate (Compound Nr. 1);
EX. 18: (D) 2-piperidino-penten-(2)-one-(4) (Compound Nr. 7).

In FIG. 3 the letters appearing on the rheometical curves indicate the following compounds with formula (I):
EX. 13: (E) ethyl β-benzylamino crotonate (Compound Nr. 2);
EX. 14: (F) 2-tert-octylamino-penten-(2)-one-(4) (Compound Nr. 3);
EX. 15: (G) 2-cyclohexylamino-penten-(2)-one-(4) (Compound Nr. 4).

In FIG. 4 the letters appearing on the rheometrical curves indicate the following compounds with formula (I):
EX. 21: (H) ethyl β-(2-methoxyethylamino)-crotonate (Compound Nr. 10);
EX. 19: (I) ethyl β-pyrrolidino crotonate (Compound Nr. 8);
EX. 20: (L) 2-pyrrolidino-penten-(2)-one-(4) (Compound Nr. 9).

TABLE 2

| Example Nr | Enamine | t$_c$ (90) |
|---|---|---|
| 11 | Absent | 9'24" |
| 12 | Compound nr 1 | 8'12" |
| 13 | Compound nr 2 | 8'12" |
| 14 | Compound nr 3 | 8'54" |
| 15 | Compound nr 4 | 8'36" |
| 16 | Compound nr 5 | 8'18" |
| 17 | Compound nr 6 | 6'12" |
| 18 | Compound nr 7 | 5'48" |
| 19 | Compound nr 8 | 5'56" |
| 20 | Compound nr 9 | 5'10" |
| 21 | Compound nr 10 | 7'18" |

What is claimed is:

1. A method for accelerating the vulcanization of a rubber composition, comprising combining a natural or synthetic rubber with an effective amount of a vulcanization accelerator, wherein said vulcanization accelerator is at least one compound selected from the group consisting of compounds belonging to the group of enamines having formula (I):

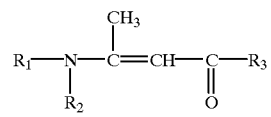

wherein:
R$_1$ and R$_2$, considered jointly with the nitrogen atom, represent a C$_3$–C$_8$ heterocyclic group, optionally containing a heteroatom selected from the group consisting of oxygen, nitrogen and sulfur; and R$_3$ represents a C$_1$–C$_{18}$ alkyl group, linear or branched; a C$_6$–C$_{18}$ aryl group; a C$_7$–C$_{20}$ alkylaryl or arylalkyl group; or a C$_1$–C$_8$ alkoxyl group linear or branched.

2. The method of claim 1, wherein said natural rubber is combined with said vulcanization accelerator.

3. The method of claim 1, wherein said synthetic rubber is combined with said vulcanization accelerator.

4. The method of claim 3, wherein said synthetic rubber is selected from the group consisting of SBR, NBR, BR and EPDM.

5. The method of claim 1, which further comprises adding mercaptobenzothiazole sulfenamide to said natural or synthetic rubber.

6. The method of claim 1, wherein in formula (I), $R_1$ and $R_2$ are each independently hydrogen, methyl, ethyl, propyl, butyl, octyl, cyclohexyl, benzyl or methoxyethyl.

7. The method of claim 1, wherein said $R_1$ and $R_2$, jointly with a nitrogen atom, represent morpholine, pyrrolidone, piperidine, piperizine, thiomorpholine, thiozolodine or benzothiazolodine groups.

8. The method of claim 1, wherein $R_3$ in the formula (I) is methyl, ethyl, propyl, phenyl, oxymethyl, or oxyethyl.

9. The method of claim 7, wherein said $R_1$ and $R_2$, jointly with the nitrogen atoms, represent a morpholine group.

10. The method of claim 7, wherein said $R_1$ and $R_2$, jointly with the nitrogen atoms, represent a piperidine group.

11. The method of claim 7, wherein said $R_1$ and $R_2$, jointly with the nitrogen atom, represent a pyrrolidone group.

12. The method of claim 1, wherein said compound of the formula (I) is selected from the group consisting of ethyl β-morpholino crotonate, ethyl β-piperidino crotonate, ethyl β-pyrrolidino crotonate, 2-piperidino-penten-(2)-one-(4), and 2-pyrrolidino-penten-(2)-one-(4).

13. The method of claim 1, wherein said effective amount of said enamine of the formula (I) is 0.5% by weight based upon the rubber.

\* \* \* \* \*